(12) United States Patent
Yoo et al.

(10) Patent No.: US 11,449,997 B2
(45) Date of Patent: Sep. 20, 2022

(54) SKIN CONDITION MEASURING MODULE

(71) Applicant: Lululab Inc., Seoul (KR)

(72) Inventors: Sang Wook Yoo, Suwon-si (KR); Yong Joon Choe, Seoul (KR)

(73) Assignee: Lululab Inc., Seoul (KR)

( * ) Notice: Subject to any disclaimer, the term of this patent is extended or adjusted under 35 U.S.C. 154(b) by 178 days.

(21) Appl. No.: 16/960,100

(22) PCT Filed: Dec. 28, 2018

(86) PCT No.: PCT/KR2018/016858
§ 371 (c)(1),
(2) Date: Jul. 6, 2020

(87) PCT Pub. No.: WO2019/139291
PCT Pub. Date: Jul. 18, 2019

(65) Prior Publication Data
US 2021/0065369 A1 Mar. 4, 2021

(30) Foreign Application Priority Data
Jan. 9, 2018 (KR) .................. 10-2018-0002898

(51) Int. Cl.
*G06T 7/00* (2017.01)
*G06T 7/80* (2017.01)
(Continued)

(52) U.S. Cl.
CPC .......... *G06T 7/0014* (2013.01); *A61B 5/0013* (2013.01); *A61B 5/0079* (2013.01); *A61B 5/441* (2013.01); *A61B 5/486* (2013.01); *A61B 5/7207* (2013.01); *A61B 5/7282* (2013.01); *G06Q 30/0631* (2013.01); *G06T 7/80* (2017.01); *G16H 30/40* (2018.01); *G16H 40/67* (2018.01); *G16H 50/20* (2018.01); *H04N 5/2351* (2013.01);
(Continued)

(58) Field of Classification Search
CPC .................................. G06T 7/0014; G06T 7/80
See application file for complete search history.

(56) References Cited

U.S. PATENT DOCUMENTS

2008/0147053 A1* 6/2008 Kang ................. G01N 21/6456
600/431
2014/0064579 A1* 3/2014 Lee ....................... G06T 7/0012
382/128
(Continued)

FOREIGN PATENT DOCUMENTS

KR 10-2005-0063781 A 6/2005
KR 10-2014-0028415 A 3/2014
(Continued)

OTHER PUBLICATIONS

International Search Report for PCT/KR2018/016858 dated Apr. 1, 2019 from Korean Intellectual Property Office.

*Primary Examiner* — Jerry T Jean Baptiste
(74) *Attorney, Agent, or Firm* — Revolution IP, PLLC (57) ABSTRACT

A skin condition measuring module according to the present invention can be designed to effectively diagnose a user's skin condition while being installed within or connected with: a kiosk; a skin condition measuring mirror; a vending machine for performing skin condition measurement and providing cosmetic products; or a module-embedded skin condition measuring device.

10 Claims, 3 Drawing Sheets

(51) Int. Cl.
  *G16H 40/67*  (2018.01)
  *G16H 50/20*  (2018.01)
  *G16H 30/40*  (2018.01)
  *A61B 5/00*  (2006.01)
  *G06Q 30/06*  (2012.01)
  *H04N 5/235*  (2006.01)
  *H04N 5/265*  (2006.01)

(52) U.S. Cl.
  CPC .......... *H04N 5/265* (2013.01); *A61B 2576/02* (2013.01); *G06T 2207/20212* (2013.01); *G06T 2207/30088* (2013.01); *G06T 2207/30201* (2013.01)

(56) References Cited

U.S. PATENT DOCUMENTS

2017/0119301 A1\* 5/2017 Kimura ................ G06T 7/0012
2018/0276732 A1\* 9/2018 Pai ........................ G16H 20/10

FOREIGN PATENT DOCUMENTS

| | | |
|---|---|---|
| KR | 10-2016-0007754 A | 1/2016 |
| KR | 10-2016-0144971 A | 12/2016 |
| KR | 10-1738417 B1 | 5/2017 |
| KR | 10-1810959 B1 | 12/2017 |

\* cited by examiner

ially, a portable device for measuring the skin condition, which captures an image of facial skin of the user to analyze various skin troubles (e.g., wrinkles, pores, acne, etc.) and the like on the user face, has been developed.

SKIN CONDITION MEASURING MODULE

TECHNICAL FIELD

This application claims the benefit of priority from Korean Patent Application No. 10-2018-0002898 filed on Jan. 9, 2018, the contents of which are incorporated herein by reference in its entirety.

The present invention relates to a skin condition measuring module.

More particularly, the present invention relates to a skin condition measuring module installed in a skin condition measuring device or configured to interwork with the skin condition measuring device to diagnose a skin condition of a user.

BACKGROUND ART

Recently, as interest in beauty increases, interest in skin care of a user face is increasing. In particular, a portable device for measuring the skin condition, which captures an image of facial skin of the user to analyze various skin troubles (e.g., wrinkles, pores, acne, etc.) and the like on the user face, has been developed.

Meanwhile, a conventional device for measuring a skin condition, which is for skin analysis, captures an image of the user face based on preset capturing parameters (e.g., an intensity or a direction of a light source, an aperture value, a shutter speed, or the like) while the user face is put in the device for measuring the skin condition.

The conventional device for measuring the skin condition has an advantage that a capturing position of the user is fixed, but it was inconvenient in terms of portability and mobility, and difficult to measure the skin condition in a place desired by the user. Also, the price of the conventional device was so expensive that it was difficult for general consumers to purchase the conventional device.

Meanwhile, a portable device for measuring a skin condition, which has portability and mobility, has been developed as a skin measuring device. However, the technology development has been limited in the field of a device for measuring a specific area of skin, and a technology for analyzing an entire face of the user and a technology for acquiring a clear user face image to measure the skin condition still have a problem to be technically solved.

(Patent Document 1) Korean Unexamined Patent Publication No. 2005-0063781

DISCLOSURE

Technical Problem

The present invention provides a skin condition measuring module configured to effectively acquire a single user face image or an entire user face image.

In addition, the present invention provides a skin condition measuring module configured to effectively acquire the entire face image by controlling a face position of a user when capturing an image of a user face.

Moreover, the present invention provides a skin condition measuring module installed in or configured to interwork with: a kiosk; a skin condition measuring mirror; a vending machine for measuring a skin condition and providing a cosmetic product; or a module-embedded skin condition measuring device so as to diagnose the skin condition of the user, and to recommend a product for improving the skin condition.

Technical Solution

To achieve the objects described above, according to the present invention, there is provided a skin condition measuring module.

The skin condition measuring module is installed in a skin condition measuring device or configured to interwork with the skin condition measuring device to diagnose a skin condition of a user, and includes a user face capturing camera control unit and a light source control unit. In addition, the skin condition measuring module includes: a memory in which software for driving the module is stored; and a processor configured to form a single user face image for measuring the skin condition, which is acquired by a user face capturing camera, or configured to form an entire user face image for measuring the skin condition by extracting specific areas of a user face from a plurality of user face images acquired based on a plurality of capturing parameters set to extract the specific areas of the user face and composing the extracted specific areas of the user face.

In one example, the processor may be configured to analyze brightness of a plurality of user face images acquired based on a plurality of preliminary capturing parameters to set one or more of the preliminary capturing parameters as the capturing parameters.

In one example, the processor may be configured to set a first preliminary capturing parameter, which allows a first area of the user face image to have a brightness value within a preset range, as a first capturing parameter, and configured to set a second preliminary capturing parameter, which allows a second area of the user face image to have a brightness value within a preset range, as a second capturing parameter.

In one example, the processor may be configured to extract a first face area from a first user face image acquired by the first capturing parameter, extract a second face area from a second user face image acquired by the second capturing parameter, and compose the first face area and the second face area to form the entire user face image for measuring the skin condition.

In one example, the processor may be configured to correct and compose the first face area and the second face area according to detected motion information.

In one example, the capturing parameters may include at least one of an intensity of a light source, a direction of the light source, a shutter speed, and an aperture value.

In addition, according to the present invention, the skin condition measuring module may further include: a sensor unit having a distance sensor for measuring a distance between the user and the camera; and an output control unit for controlling an output device which is configured to suggest the user to move a face position when a partial area of the user face deviates from the user face image acquired by the user face capturing camera, suggest the user to move the face position when the distance between the user and the camera, which is measured by the distance sensor for measuring the distance between the user and the camera, deviates from a preset value, or suggest the user to move the face position when the partial area of the user face deviates from the user face image acquired by the user face capturing camera, and the distance between the user and the camera, which is measured by the distance sensor for measuring the distance between the user and the camera, deviates from the preset value.

In one example, the processer may be configured to analyze the formed single user face image or the formed entire user face image so as to provide a skin condition diagnosis result, and recommend a product for improving the skin condition of the user based on the skin condition diagnosis result.

In addition, the skin condition measuring module may further include a communication control unit for controlling a communication device for transmitting the single user face image or the entire user face image to an external user terminal.

The skin condition measuring module may further include an external terminal connected to or configured to interwork with the skin condition measuring device.

In one example, the skin condition measuring device in which the skin condition measuring module is installed or with which the skin condition measuring module is configured to interwork may include: a kiosk; a skin condition measuring mirror; a vending machine for measuring the skin condition and providing a cosmetic product; or a module-embedded skin condition measuring device.

Advantageous Effects

According to the present invention, the skin condition measuring module is installed in a skin condition measuring device or configured to interwork with the skin condition measuring device so as to effectively acquire a single user face image or an entire user face image and to accurately analyze a skin condition of a user based on the acquired user face image.

In addition, when the skin condition measuring module according to the present invention is used, the user face image can be effectively acquired by controlling a face position of the user when capturing an image of the user face.

Moreover, according to the present invention, the skin condition measuring module can be applied to a portable or non-portable skin condition measuring device such as a kiosk; a skin condition measuring mirror; a vending machine for measuring a skin condition and providing a cosmetic product; or a module-embedded skin condition measuring device without limitation so as to effectively diagnose the skin condition of the user and perform a product recommendation function.

However, the scope of the present invention is not limited by the above effects.

MODE FOR INVENTION

Best Mode

Hereinafter, the present invention will be described in more detail with reference to the drawings and examples.

In the present specification, a singular expression includes a plural expression unless otherwise specified.

Although the terms used in the present specification are preferably selected from general terms that are widely used at present under the consideration of functions in the present invention, the terms may vary according to the intention of those of ordinary skill in the art, judicial precedents, or introduction of new technology. In addition, in a specific case, some terms may be arbitrarily selected by the applicant, and in this case, the meaning of the terms will be described in detail in a corresponding part of the detailed description of the invention. Therefore, the terms used in the present disclosure should be defined based on the meaning of the terms and the contents throughout the present disclosure, not by the simple names of the terms.

The present invention may have various embodiments, and the embodiments may be variously modified. Specific embodiments will be illustrated in the drawings and described in detail in the detailed description. However, it should be understood that the scope of the present invention is not limited to the specific embodiments, and includes all modifications, equivalents, or substitutes within the technical idea and technical scope of the present invention. While describing the embodiments, the detailed description of the publicly-known related art will be omitted when they are determined to make the subject matter rather unclear.

Although terms such as 'first' or 'second' may be used herein to describe various elements, the elements should not be limited by the terms. The terms are used only to distinguish one element from another element.

In the present specification, a singular expression includes a plural expression unless the context clearly indicates otherwise.

In the present specification, the term such as 'include' or 'consist of' is intended to designate the presence of characteristics, numbers, steps, operations, elements, parts, or combinations thereof disclosed herein, and shall not be construed to preclude any possibility of the presence or addition of one or more other characteristics, numbers, steps, operations, elements, parts, or combinations thereof.

Hereinafter, a skin condition measuring module according to the present invention will be described in more detail with reference to the accompanying drawings.

The present invention relates to a skin condition measuring module. The skin condition measuring module according to the present invention may be installed in a skin condition measuring device or configured to interwork with the skin condition measuring device to diagnose a skin condition of a user. The skin condition measuring device may be understood as encompassing a portable or non-portable skin condition measuring device.

In one example, the skin condition measuring device may include: a kiosk; a skin condition measuring mirror; a vending machine for measuring a skin condition and providing a cosmetic product; or a module-embedded skin condition measuring device. Therefore, the skin condition measuring module according to the present invention may be installed in or configured to interwork with the portable or non-portable skin condition measuring device without limitation so as to diagnose the skin condition of the user.

The inventor of the present invention has made the present invention by developing a module including a processor capable of effectively acquiring a user face image regardless of a size of the skin condition measuring device.

In addition, the inventor of the present invention has developed a skin condition measuring module capable of accurately diagnosing the skin condition and recommending a related product, so that processes of diagnosing the skin condition and recommending the related product may be unified.

Figure 1:
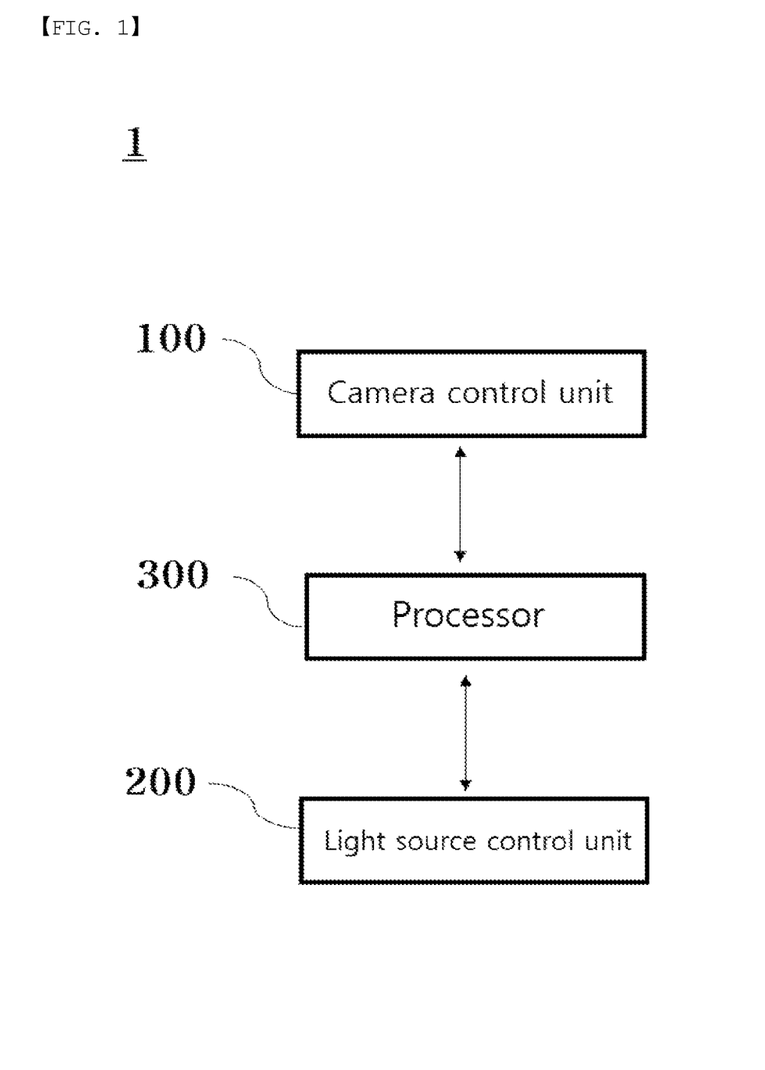
FIGS. 1 to 3 are block diagrams showing a configuration of a skin condition measuring module according to the present invention.

FIG. 1 is a block diagram showing components of a skin condition measuring module according to the present invention.

As shown in FIG. 1, a skin condition measuring module 1 may include a user face capturing camera control unit 100 and a light source control unit 200. In addition, the skin condition measuring module 1 may include: a memory 300 in which software for driving the module is stored; and a processor 400 configured to form a single user face image for measuring the skin condition, which is acquired by a user face capturing camera, or configured to form an entire user face image for measuring the skin condition by extracting specific areas of a user face from a plurality of user face images acquired based on a plurality of capturing parameters set to extract the specific areas of the user face and composing the extracted specific areas of the user face.

As used herein, the term "single user face image" refers to a single image acquired by a camera to analyze the skin condition and formed by the processor, and the term is used herein in order to differentiate the single user face image from the entire user face image which is formed through a technology of extracting and composing specific areas of the user face images acquired based on the capturing parameters.

As used herein, the term "entire user face image" refers to a user face image which is formed through a technology of extracting specific face areas from the user face images acquired based on the capturing parameters and composing the specific face areas, and used to measure the skin condition.

The user face capturing camera control unit according to the present invention may control the user face capturing camera for capturing an image of the user face.

In one example, the camera control unit may control the camera for acquiring the user face image by capturing the image of the user face based on an arbitrary capturing parameter. In this case, the user face image may be formed as the single user face image by the processor.

In another example, the camera control unit may control the camera for acquiring a plurality of images by capturing images of the user face based on the capturing parameters.

In detail, the camera control unit may control various capturing conditions of the user face capturing camera capable of acquiring the user face images by capturing the images of the user face multiple times based on the arbitrary capturing parameter.

In more detail, the camera may acquire a plurality of images by capturing the images of the user face based on the capturing parameters. The user face capturing camera control unit may control the camera capable of acquiring the images by capturing the images of the user face multiple times based on different capturing parameters (an intensity of a light source unit, a shutter speed value, an aperture value, or the like).

The skin condition measuring module may include the light source control unit. The light source control unit may control a light source unit including at least one light source. In detail, the light source may provide light toward the user face, and may emit, for example, at least one of red light, green light, and blue light such that white light may be emitted from the light source unit. The light source control unit may control an intensity and a wavelength of the light source.

In addition, the skin condition measuring module according to the present invention may include the memory 300. The memory 300 may include various software for driving the module in the skin condition measuring device.

For example, the memory 170 may store software configured to implement sensing, communication, presentation, web browser, and service functions.

As described above, the memory 170 may include various programs, but the various programs may be partially omitted, modified, or added depending on a type and characteristics of the mounting or interworking skin condition measuring device.

The skin condition measuring module may include the processor. The processor may be configured to interwork with various control units in the module to set overall conditions of the module.

Figure 2:
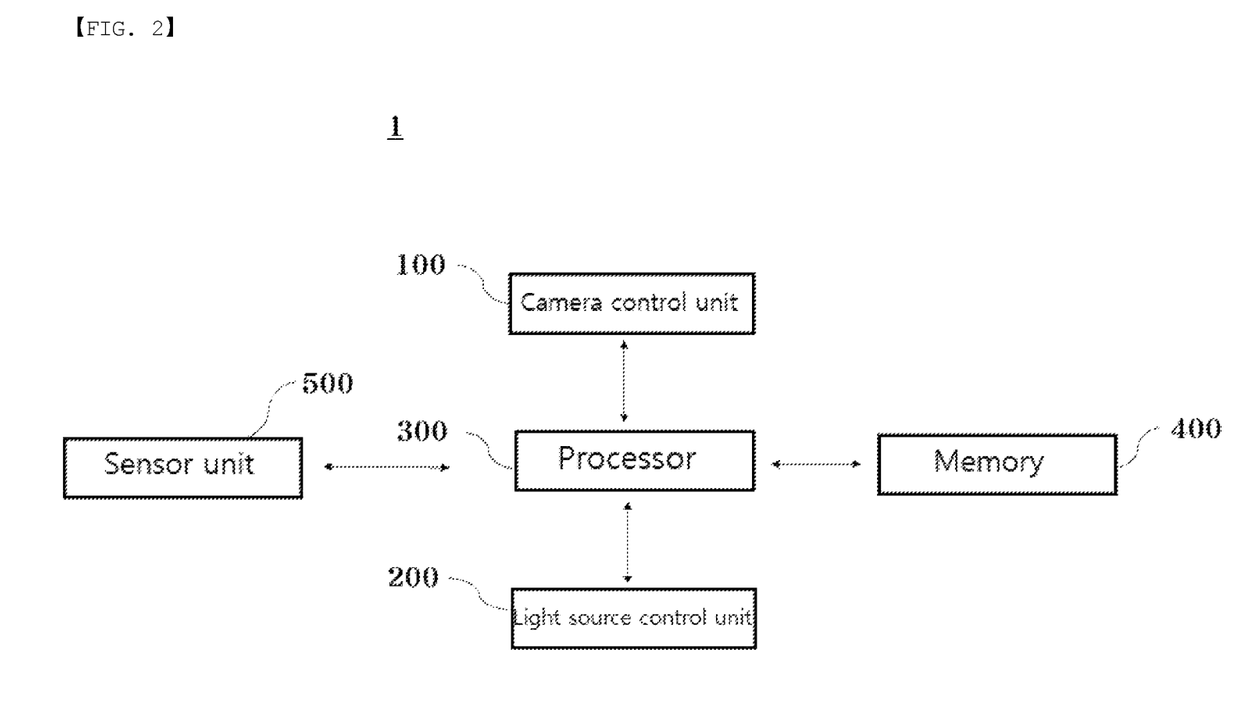
Figure 3:
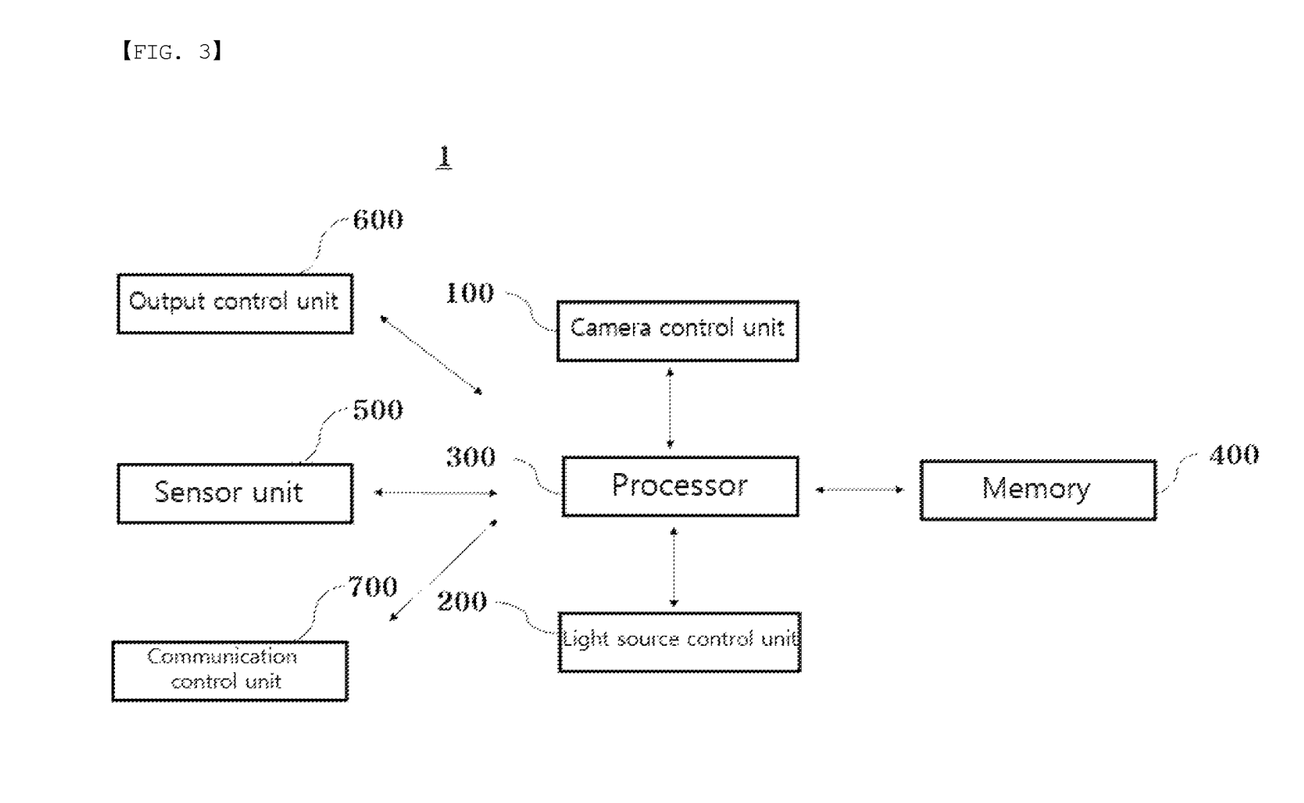

In other words, as shown in FIGS. 1 to 3, each individual component of the skin condition measuring module according to the present invention may be controlled and operated by the processor 400.

The processor may be, especially among various control operations, configured to form the single user face image for measuring the skin condition, which is acquired by the user face capturing camera, or configured to form the entire user face image for measuring the skin condition by extracting the specific areas of the user face from the user face images acquired based on the capturing parameters set to extract the specific areas of the user face and composing the extracted specific areas of the user face.

In one example, the processor may analyze brightness of the user face image acquired based on a preliminary capturing parameter, and set the preliminary capturing parameter as the capturing parameter. At this time, the preliminary capturing parameter may be determined according to an external lighting environment. In this case, the processor may acquire the user face image based on the capturing parameter set based on the preliminary capturing parameter, and set the user face image as the single user face image for measuring the skin condition.

In another example, the processor may be configured to form the entire user face image for measuring the skin condition by extracting the specific areas of the user face from the user face images acquired based on the capturing parameters set to extract the specific areas of the user face and composing the extracted specific areas of the user face.

The capturing parameters for analyzing facial skin of the user may be set by the processor. The capturing parameter may be, for example, an intensity of the light source unit and/or a direction of the light source unit set by the light source control unit, or may be a shutter speed and/or an aperture value set by the camera control unit.

In one example, the capturing parameters may include at least one of an intensity of a light source, a direction of the light source, a shutter speed, and an aperture value.

Hereinafter, an operation of the processor configured to extract the specific areas of the user face based on a plurality of preliminary capturing parameters and compose the specific areas to form the entire user face image for measuring the skin condition will be described in more detail.

The processor may be configured to analyze brightness of a plurality of user face images acquired based on a plurality of preliminary capturing parameters to set one or more of the preliminary capturing parameters as the capturing parameters.

In one example, when an image captured based on a first preliminary capturing parameter among the preliminary capturing parameters has a brightness value within a preset range in a first area (e.g., a face center area) of the user face, the processor may be configured to set the first preliminary capturing parameter as a first capturing parameter corresponding to the first area of the user face. In addition, when an image captured based on a second preliminary capturing parameter among the preliminary capturing parameters has a brightness value within a preset range in a second area (e.g., a face outer periphery area) of the user face, the processor may be configured to set the second preliminary capturing parameter as a second capturing parameter corresponding to the second area of the user face.

In other words, the processor may be configured to set the first preliminary capturing parameter, which allows the first area of the user face image to have the brightness value within the preset range, as the first capturing parameter, and set the second preliminary capturing parameter, which allows the second area of the user face image to have the brightness value within the preset range, as the second capturing parameter.

Based on the capturing parameters, the processor may be configured to extract the specific areas of the user face from the user face images acquired based on the set capturing parameters.

In one example, the processor may be configured to acquire a first user face image by capturing an image of the user face based on the first capturing parameter, and acquire a second user face image by capturing an image of the user face based on the second capturing parameter. In addition, the processor may be configured to extract user face areas corresponding to a plurality of images from the images, and compose the extracted user face areas to acquire an entire face image.

In other words, the processor may be configured to extract a first face area from the first user face image acquired by the first capturing parameter, and extract a second face area from the second user face image acquired by the second capturing parameter. In addition, the processor may be configured to compose the first face area and the second face area to form the entire user face image for measuring the skin condition.

If the skin condition measuring module is installed in or configured to interwork with the portable skin condition measuring device, the processor may correct and compose the first face area and the second face area according to detected motion information of the portable skin condition measuring device. In other words, when a motion of the portable skin condition measuring device in which the module including the processor is installed or with which the module including the processor is configured interwork is detected while capturing the second user face image, the processor may correct the second face area according to the detected motion of the device. According to another embodiment, the processor may correct the second user face image before extracting the second face area according to the motion of the portable skin condition measuring device in which the module including the processor is installed or with which the module including the processor is configured interwork. The detection of the motion may be, for example, performed by a sensor unit that will be described below.

In addition, when composing the first face area and the second face area, the processor may be configured to perform brightness correction to compose the first face area and the second face area.

In detail, the processor may be configured to determine a brightness difference value between the first face area and the second face area in the vicinity of a boundary between the first face area and the second face area. In addition, the processor may be configured to determine a composition weight for at least one of the first face area and the second face area based on the brightness difference value. In this case, the composition weight may be a weight for adjusting the brightness. Further, the processor may be configured to adjust brightness of at least one of the first face area and the second face area based on the composition weight, and to compose the first face area and the second face area.

Through the configuration of the processor as described above, the entire user face image for more accurately measuring the skin condition may be acquired.

In addition, the skin condition measuring module according to the present invention may further include a sensor unit and an output control unit.

In other words, as shown in FIG. 2, the skin condition measuring module according to the present invention may further include: a sensor unit 500 having a distance sensor for measuring a distance between the user and the camera; and an output control unit 600 for controlling an output device which is configured to suggest the user to move a face position when a partial area of the user face deviates from the user face image acquired by the user face capturing camera, suggest the user to move the face position when the distance between the user and the camera, which is measured by the distance sensor for measuring the distance between the user and the camera, deviates from a preset value, or suggest the user to move the face position when the partial area of the user face deviates from the user face image acquired by the user face capturing camera, and the distance between the user and the camera, which is measured by the distance sensor for measuring the distance between the user and the camera, deviates from the preset value.

The output control unit 600 included in the skin condition measuring module according to the present invention may control an output device. The output device may suggest the user to move a face position when a partial area of the user face deviates from the user face image acquired by the user face capturing camera, suggest the user to move the face position when the distance between the user and the camera, which is measured by the distance sensor for measuring the distance between the user and the camera, deviates from a preset value, or suggest the user to move the face position when the partial area of the user face deviates from the user face image acquired by the user face capturing camera, and the distance between the user and the camera, which is measured by the distance sensor for measuring the distance between the user and the camera, deviates from the preset value. The output control unit may control the suggestion to move the face position by the output device.

The skin condition measuring module according to the present invention can effectively acquire the user face image without deviation through the configuration of the output control unit that controls the output device for performing the suggestion for the user to move the face position.

The suggestion for the user to move the face position may be performed when the partial area of the user face deviates from the user face image acquired by the user face capturing camera and/or when the distance between the user and the camera measured by the distance sensor included in the sensor unit to measure the distance between the user and the camera deviates from the preset value.

In one example, the suggestion for the user to move the face position by the output device may be performed when the partial area of the user face deviates from the user face image acquired by the user face capturing camera, and the output control unit may control such an operation of the output device.

In the above description, a deviation degree of the user face area may be, for example, determined based on data stored in sensing software stored in the memory.

In more detail, the deviation degree of the user face area may be determined based on a case in which detection of a face outer periphery of the user fails or the face outer periphery is cropped off at the boundary when the face outer periphery of the user is detected from the user face image. In this case, the face outer periphery may be acquired through a landmark detection technology, an edge detection technology, or the like.

In another example, the suggestion for the user to move the face position by the output device may be performed when the distance between the user and the camera, which is measured by the distance sensor for measuring the distance between the user and the camera, deviates from the preset value. In this case, the output control unit may control the output device.

The sensor unit having the distance sensor for measuring the distance between the user and the camera may include, for example, a distance sensor such as an ultrasonic sensor or a time-of-flight (ToF) sensor, but embodiments are not limited thereto.

The output control unit may control the output device that suggests the user to move the face position when the distance between the user and the camera measured by the sensor unit deviates from the preset value.

In a more specific example, the distance sensor of the sensor unit may measure the distance between the user and the camera, and a measurement result of the distance sensor may be used in association with the sensing software of the memory so that the suggestion to move the face position by the output device may be performed through the output control unit.

Meanwhile, the sensor unit may detect an external lighting device to determine the preliminary capturing parameters including: the intensity and the direction of the light source unit; and the shutter speed, the aperture value, an exposure value, and the like of the camera, and may serve to detect the motion information of the skin condition measuring device in which the module is installed or with which the module is configured interwork as described above. Therefore, in addition to the distance sensor, the sensor unit may further include a motion sensor (e.g., an acceleration sensor, a gyro sensor, an electromagnetic sensor, etc.) and the like.

In another example, the output control unit may control the output device that suggests the user to move the face position when the partial area of the user face deviates from the user face image acquired by the user face capturing camera, and the distance between the user and the camera, which is measured by the distance sensor for measuring the distance between the user and the camera, deviates from the preset value.

As described above, through the configurations of the sensor unit including the distance sensor and the output control unit, the skin condition measuring module capable of preventing an inaccurate face image from being acquired due to the deviation of the user face in advance and capable of acquiring a clear user face image may be provided.

The output control unit may control, for example, a display and/or an audio output device.

In detail, the output control unit may control a display that performs the suggestion to move the face position. Meanwhile, the display may display various image data and a user interface (UI) in addition to the suggestion to move the face position.

In addition, the output control unit may control an audio output device that performs the suggestion to move the face position through a voice. Meanwhile, the audio output device may output various notification sounds or voice messages in addition to the suggestion to move the face position.

In another example, the output control unit may control an arrow indicating a preferred direction to move the face position or a light emitting diode (LED) implementing a specific color.

Meanwhile, the skin condition measuring module according to the present invention may be installed in or configured to interwork with a predetermined skin condition measuring device to autonomously analyze the entire user face image.

In one example, the processer may be configured to analyze the formed single user face image or the formed entire user face image so as to provide a skin condition diagnosis result, and recommend a product for improving the skin condition of the user based on the skin condition diagnosis result.

The recommendation on the product for improving the skin condition may be performed through a process and related software thereof for crawling online web pages to collect cosmetic product-related review data, extracting a list of key words related to evaluation for a cosmetic product within the collected data through natural language processing, training a model for quantifying cosmetic product preferences through machine learning based on the extracted list of key words, calculating a cosmetic product preference score for new cosmetic product-related review data based on the model trained by a model learning unit, and recommending a cosmetic product according to the cosmetic product preference score calculated by a preference calculation unit, but embodiments are not limited thereto.

In addition, after the single user face image or the entire user face image formed by the processor is transmitted to a predetermined user terminal, the single user face image or the entire user face image may be analyzed through the user terminal. In this case, the skin condition measuring module may further include a communication control unit for controlling a communication device.

The communication control unit may be, for example, controlled to receive a request to capture the image of the user face from an external user terminal, and may be controlled to transmit the single user face image or the entire user face image to the external user terminal. In this case, the communication control unit may control the communication device implemented as a Bluetooth module, but this is only an example. The communication control unit may control various communication devices such as a ZigBee communication module, a Wi-Fi communication module, or an NFC communication module.

Meanwhile, the skin condition measuring module has been described in the above embodiment as transmitting the single user face image or the entire user face image to the external user terminal, but this is only an example. In addition, the skin condition measuring module may transmit each of the user face images acquired based on the capturing parameters to the external user terminal. In this case, the user terminal may analyze the skin condition of the user face by extracting and composing the specific face areas of the user face images in the same manner as the above-described operation performed by the processor.

In addition, as described above, the processor may directly analyze the single user face image or the entire user face image to acquire skin condition information on at least one of pigmentation, acne, sebum, pores, and wrinkles on the user face, and may output the acquired skin condition information through the output device controlled by the output control unit.

Further, the present invention may further include an input control unit for controlling an input unit. The input control unit may control the input unit configured to receive a user command for operating the mounting or interworking skin condition measuring device to transmit information on the user command to the processor. Meanwhile, the input unit may vary depending on the type of the skin condition measuring device, and may include, for example, a touch panel for detecting a touch of the user, a (digital) pen sensor, or the like.

In addition, the skin condition measuring module according to the present invention may further include an external terminal connected to or configured to interwork with the skin condition measuring device. The external terminal may be, for example, a USB terminal, but is not limited thereto. The external terminal may allow the mounting or interworking skin condition measuring device and the skin condition measuring module to be electrically connected to each other to measure the skin condition, and there is no limitation on a type of the external terminal.

Meanwhile, the skin condition measuring device may include: a kiosk; a skin condition measuring mirror; a vending machine for measuring the skin condition and providing a cosmetic product; or a module-embedded skin condition measuring device.

In one example, when the skin condition measuring device is a kiosk, the skin condition measuring module may be embedded in a bezel of the kiosk, and may be connected to a kiosk PC in a wired manner through the external terminal so as to measure the skin condition and recommend the related product as described above.

In another example, when the skin condition measuring device is a portable skin condition measuring device, the skin condition measuring module may be installed in the skin condition measuring device to acquire the single user face image or acquire the entire user face image by capturing, extracting, and composing a plurality of user face images, and skin condition analysis and customized product recommendation may be performed by the measuring device or through the external user terminal based on the single user face image or the entire user face image.

In still another example, when the skin condition measuring device is a skin condition measuring mirror, the skin condition measuring module may be installed in the mirror or disposed outside the mirror depending on a structure or a driving configuration of the mirror, and may electrically interwork with the mirror to perform skin condition measurement and customized product recommendation.

As described above, although the present disclosure has been described with limited embodiments and drawings, the present disclosure is not limited to the above embodiments, and various changes and modifications can be made from the above description by those skilled in the art to which the present disclosure pertains. Therefore, the scope of the present disclosure should not be limited to the above-described embodiments, but should be defined by the appended claims and their equivalents.

The invention claimed is:

1. A skin condition measuring module installed in a skin condition measuring device or configured to interwork with the skin condition measuring device to diagnose a skin condition of a user, and including a user face capturing camera control unit and a light source control unit, the skin condition measuring module comprising:
   a memory in which software for driving the module is stored;
   a processor configured to form a single user face image for measuring the skin condition, which is acquired by a user face capturing camera, or configured to form an entire user face image for measuring the skin condition by extracting specific areas of a user face from a plurality of user face images acquired based on a plurality of capturing parameters set to extract the specific areas of the user face and composing the extracted specific areas of the user face;
   a sensor unit having a distance sensor for measuring a distance between the user and the camera; and
   an output control unit for controlling an output device which is configured to suggest the user to move a face position when a partial area of the user face deviates from the user face image acquired by the user face capturing camera, suggest the user to move the face position when the distance between the user and the camera, which is measured by the distance sensor for measuring the distance between the user and the camera, deviates from a preset value, or suggest the user to move the face position when the partial area of the user face deviates from the user face image acquired by the user face capturing camera, and the distance between the user and the camera, which is measured by the distance sensor for measuring the distance between the user and the camera, deviates from the preset value.

2. The skin condition measuring module of claim 1, wherein the processor is configured to analyze brightness of a plurality of user face images acquired based on a plurality of preliminary capturing parameters to set one or more of the preliminary capturing parameters as the capturing parameters.

3. The skin condition measuring module of claim 2, wherein the processor is configured to set a first preliminary capturing parameter, which allows a first area of the user face image to have a brightness value within a preset range, as a first capturing parameter, and configured to set a second preliminary capturing parameter, which allows a second area of the user face image to have a brightness value within a preset range, as a second capturing parameter.

4. The skin condition measuring module of claim 3, wherein the processor is configured to extract a first face area from a first user face image acquired by the first capturing parameter, extract a second face area from a second user face image acquired by the second capturing parameter, and compose the first face area and the second face area to form the entire user face image for measuring the skin condition.

5. The skin condition measuring module of claim 4, wherein the processor is configured to correct and compose the first face area and the second face area according to detected motion information.

6. The skin condition measuring module of claim 1, wherein the capturing parameters include at least one of an intensity of a light source, a direction of the light source, a shutter speed, and an aperture value.

7. The skin condition measuring module of claim 1, wherein the processer is configured to analyze the formed single user face image or the formed entire user face image so as to provide a skin condition diagnosis result, and recommend a product for improving the skin condition of the user based on the skin condition diagnosis result.

8. The skin condition measuring module of claim 1, further comprising a communication control unit for controlling a communication device for transmitting the single user face image or the entire user face image to an external user terminal.

9. The skin condition measuring module of claim 1, further comprising an external terminal connected to or configured to interwork with the skin condition measuring device.

10. The skin condition measuring module of claim 1, wherein the skin condition measuring device includes: a kiosk; a skin condition measuring mirror; a vending machine for measuring the skin condition and providing a cosmetic product; or a module-embedded skin condition measuring device.

\* \* \* \* \*